(12) United States Patent
Deckers

(10) Patent No.: US 9,465,069 B2
(45) Date of Patent: Oct. 11, 2016

(54) METHOD FOR THE EXTRACTION OF RECOMBINATION CHARACTERISTICS AT METALLIZED SEMICONDUCTOR SURFACES

(71) Applicants: IMEC VZW, Leuven (BE); Katholieke Universiteit Leuven, KU LEUVEN R&D, Leuven (BE)

(72) Inventor: Jan Deckers, Leuven (BE)

(73) Assignees: IMEC VZW, Leuven (BE); Katholieke Universiteit Leuven, KU Leuven R&D, Leuven (BE)

( * ) Notice: Subject to any disclaimer, the term of this patent is extended or adjusted under 35 U.S.C. 154(b) by 238 days.

(21) Appl. No.: 14/495,607

(22) Filed: Sep. 24, 2014

(65) Prior Publication Data

US 2015/0084661 A1    Mar. 26, 2015

(30) Foreign Application Priority Data

Sep. 24, 2013 (EP) .................................... 13185659

(51) Int. Cl.
*G01N 21/64* (2006.01)
*G01R 31/265* (2006.01)
*H01L 21/66* (2006.01)
*G01R 31/40* (2014.01)
*G01N 21/63* (2006.01)
*G01N 33/00* (2006.01)

(52) U.S. Cl.
CPC ........... *G01R 31/2656* (2013.01); *G01N 21/63* (2013.01); *G01N 21/6408* (2013.01); *G01N21/6489* (2013.01); *G01N 33/00* (2013.01); *H01L 22/14* (2013.01); *H01L 22/34* (2013.01); *H02S 50/00* (2013.01); *G01N 2033/0095* (2013.01)

(58) Field of Classification Search
CPC ...................... G01N 2033/0095; G01N 21/63; G01N 21/6408; G01N 21/6489; G01N 33/00; G01N 33/005; G01R 31/2656; H01L 22/14; H01L 22/34; H01L 21/0242; H01L 21/02458; H01L 21/0254; H01L 21/02576; H01L 21/02631; H01L 33/007; H02S 50/00

USPC ............ 324/754.21, 754.23, 762.01, 762.05; 257/94, 97

See application file for complete search history.

(56) References Cited

U.S. PATENT DOCUMENTS 5,081,414 A * 1/1992 Kusama ............. G01R 31/2656
                                                                324/642
2010/0001292 A1* 1/2010 Yamasaki ......... H01L 21/02376
                                                                257/77

FOREIGN PATENT DOCUMENTS

| EP | 2037288 A1 | 3/2009 |
|----|------------|--------|
| JP | 2-91957 | 3/1990 |
| JP | 2010-177241 | 8/2010 |
| WO | 2013/016469 A1 | 1/2013 |

OTHER PUBLICATIONS

European Search Report, European Patent Application No. 13185659.3 dated Aug. 21, 2014.
Huang, Liang et al., "Amorphous Silicon Solar Cells Using Metallic Fishnet Nanostructures Simultaneously for Schottky Contact and Plasmonics Enhancement", IEEE 9th Photovoltaic Specialists Conference, Jun. 16-21, 2013, pp. 1353-1356.

* cited by examiner

*Primary Examiner* — Vincent Q Nguyen
(74) *Attorney, Agent, or Firm* — McDonnell Boehnen Hulbert & Berghoff LLP

(57) ABSTRACT

The present disclosure relates to methods for determining recombination characteristics at metallized semiconductor surfaces and of metallized semiconductor junctions, based on photo-conductance decay measurements. Dedicated test structures are used comprising a plurality of metal features in contact with a semiconductor surface at predetermined locations, the metal features being provided in a plurality of zones, each of the plurality of zones having a different metal coverage. The method comprises performing a photo-conductance decay measurement in each of the plurality of zones, thereby determining effective lifetimes for different injection levels as a function of metal coverage; and extracting the recombination characteristics from the determined effective lifetimes.

14 Claims, 5 Drawing Sheets

METHOD FOR THE EXTRACTION OF RECOMBINATION CHARACTERISTICS AT METALLIZED SEMICONDUCTOR SURFACES

CROSS-REFERENCE TO RELATED APPLICATION

This application claims priority to European Patent Application No. 13185659.3 filed on Sep. 24, 2013, the contents of which are hereby incorporated by reference.

FIELD

The present disclosure relates to methods for the extraction of recombination characteristics at metallized semiconductor surfaces and of metallized semiconductor junctions, such as p-n junctions or high/low junctions, based on photo-conductance decay measurements.

Methods of the present disclosure may, for example, be used for determining recombination characteristics of passivated emitter and/or base contacts of photovoltaic cells.

BACKGROUND

In silicon based devices such as silicon photovoltaic cells, the metal-silicon interface at the metal contacts provides a highly recombination active surface for minority charge carriers. This may result in recombination currents and degradation of the device performance. For example, the open-circuit voltage $V_{oc}$ of photovoltaic cells decreases with increasing recombination at the metal contacts. Reduction of recombination currents at metal contacts is considered to be a critical aspect of enhancing efficiencies of highly efficient silicon photovoltaic cells.

The saturation current density of metallized semiconductor (e.g., silicon) junctions is a measure for the magnitude of the recombination current and thus for the effective surface recombination velocity of the metallized junction.

Recombination at a metal-emitter interface of a silicon photovoltaic cell, for example, may be determined by extracting the saturation current density of the metallized emitter from $J_{sc}$-$V_{oc}$ (short circuit current density—open circuit voltage) measurements and from dark current measurements as a function of metal coverage. Such measurements may need to be done at a device level, which means that it may only be possible to do the measurements on finished devices. This is generally a disadvantage since devices may be complicated and may require many process steps to finish. Using this method, it may not be possible to separate the influence of individual process steps on the recombination at the metal contacts.

It may be desirable to be able to determine surface recombination characteristics at metallized surfaces without the need for full device processing. This would allow gathering recombination information at different stages of the processing and separating the influence of individual process steps on the recombination characteristics. Exact knowledge of the injection level is important for such measurements, since various contributions to the recombination current are injection level dependent.

Photoluminescence measurements can be done at different stages of the processing and have the advantage of spatial resolution, but obtaining information on the injection level may only be possible by using complicated algorithms. This can compromise the reliability of saturation currents extracted using such techniques.

Photo-conductance decay measurements allow for effective lifetime extraction at different injection levels. Such measurements have been used for the determination of the (emitter) saturation current density at high injection levels. When using this approach for the measurement of the saturation current density at a metal/silicon interface, care should be taken to prevent wafer conductivity to be dominated by the metal layer. Therefore, a very thin metal layer (e.g., an Al layer with a thickness of about 1 nm) can be used to permit a photo-conductance decay measurement on such structures. It is a disadvantage that such thin aluminum layers may be fully oxidized before measurements are done, since aluminum is known to react with oxygen in ambient air to form aluminum oxide. Furthermore, there are many metallization techniques that do not allow for the deposition of such thin metal layers.

Photo-conductance calibrated photoluminescence imaging has been used for the local determination of saturation current densities of highly doped regions in silicon wafers, as reported by J. Mueller et al. in "Reverse saturation current density imaging of highly doped regions in silicon: A photoluminescence approach," Solar Energy Materials & Solar Cells 106 (2012) 76-79. The saturation current density is determined under high injection conditions based on photo-conductance calibrated photoluminescence images acquired at different high injection levels. By providing an optical short pass filter in front of the camera detecting the luminescence photons, the technique can also be applied to partially metallized samples. Using this measurement method the recombination at metal contacts to highly doped silicon can be quantified. It is a disadvantage of this method that saturation currents can only be extracted at high injection levels, and that the determination of injection levels requires calibration with contactless photo-conductance decay measurements and the use of both long and short wavelength pass filters in front of the detector. The thinner the wafer, the shorter the wavelength at which the cut-off needs to be made. Therefore, the method may not be suitable for measurements on thin wafers.

SUMMARY

The present disclosure provides methods for the extraction of recombination characteristics at metallized semiconductor surfaces from photo-conductance decay measurements, wherein the methods can be used at arbitrary injection levels, for instance, at high injection levels and/or at low injection levels.

The present disclosure provides methods for the extraction of recombination characteristics at metallized semiconductor surfaces from photo-conductance decay measurements, wherein the need for using a very thin metal layer can be avoided.

In the context of the present disclosure, a recombination characteristic can, for example, comprise a saturation current density, an upper limit or a lower limit of a saturation current density, a surface recombination velocity, an upper limit or a lower limit of a surface recombination velocity, and/or an (inverse) effective lifetime.

In the context of the present disclosure, a metallized semiconductor surface may be a semiconductor surface covered by a metal layer, wherein the metal layer is in direct physical contact with the semiconductor surface. In the context of the present disclosure, a metallized semiconductor surface may also be a semiconductor surface covered by a stack comprising a thin passivation layer (e.g., having a thickness less than about 5 nm) and a metal layer (also referred to as a passivated contact), wherein the passivation layer is sufficiently thin to enable an electrical contact between the semiconductor and the metal, e.g., sufficiently thin to allow a tunnel current passing through the thin passivation layer. For example, the stack may comprise a dielectric layer, e.g., silicon oxide layer, and a metal layer. For example, the stack may comprise a dielectric layer (e.g., aluminum oxide layer), a poly-silicon layer (e.g., $p^{++}$ poly-silicon) and a metal layer (e.g., aluminum layer). For example, the stack may comprise an amorphous silicon layer and a metal layer.

This disclosure is related to methods for the determination of injection dependent recombination characteristics at metallized semiconductor surfaces, such as metallized silicon surfaces, based on effective lifetime measurements as a function of metal contact area coverage. The present disclosure is further related to methods for the determination of saturation current densities of metal contacted junctions at high injection levels based on effective lifetime measurements.

A method for determining a recombination characteristic at a semiconductor surface according to embodiments of the present disclosure includes providing a test structure. In one example, the test structure comprises a semiconductor substrate having a first surface and a second surface opposite to the first surface, a first passivation layer on the first surface, a second passivation layer on the second surface, the second passivation layer having a plurality of openings at predetermined locations, and a plurality of metal features in (electrical) contact with the second semiconductor surface at the predetermined locations, thus forming metallized surfaces at the predetermined locations and non-metallized outside the predetermined locations. In this example, a characteristic size of the metal features is smaller than an effective diffusion length in the underlying semiconductor at the predetermined locations and the metal features are provided with a spacing smaller than an effective diffusion length in the underlying semiconductor outside the predetermined locations. The metal features may be grouped in a plurality of zones, wherein each of the plurality of zones has a different metal coverage. The method further includes performing a photo-conductance decay measurement in each of the plurality of zones, thereby determining effective lifetimes for different injection levels as a function of metal coverage, and extracting the recombination characteristic from the measured effective lifetimes. In the context of this example, the metal coverage is defined as the ratio between the contacted area (metallized surface area) and the total area of a zone.

In embodiments of the present disclosure, the first passivation layer of the test structure may be a continuous layer covering the first surface. In other embodiments, the first passivation layer of the test structure may have a plurality of openings at predetermined locations (as for the second passivation layer), and a plurality of metal features in contact with the first semiconductor surface at the predetermined locations. In such embodiments it is preferred to align the plurality of metal features in contact with the first surface to the plurality of metal features in contact with the second surface. It may be an advantage of using a continuous first passivation layer covering the first surface that there is no need for performing such alignment.

In a method of the present disclosure, extracting the recombination characteristic from the measured effective lifetimes may comprise determining a difference between the recombination characteristic at a metallized surface and the recombination characteristic at a non-metallized surface for each of the injection levels from a slope of a linear fit of inverse effective lifetime versus metal coverage. This difference may be considered as a lower limit for the recombination characteristic at the metallized surface.

The method may further comprise determining an upper value (estimate) of the recombination characteristic at a non-metallized surface and/or determining a lower value (estimate) of the recombination characteristic at a metallized surface for each of the injection levels from a slope of a linear fit of inverse effective lifetime versus metal coverage.

Extracting the recombination characteristic in a method of the present disclosure may comprise determining an upper limit of the recombination characteristic at a non-metallized surface from an intercept with a zero metal coverage axis of a linear fit of the inverse effective lifetime versus metal coverage.

In embodiments of the present disclosure, the recombination characteristic may be a surface recombination velocity, an inverse lifetime, or a saturation current density.

In embodiments of the present disclosure the semiconductor substrate of the test structure may comprise a first doped region forming a first p-n junction underlying the first surface and/or a second doped region forming a second p-n junction underlying the second surface.

In embodiments of the present disclosure the semiconductor substrate of the test structure may comprise a doped region forming a first high-low junction underlying the first surface and/or a second doped region forming a second high-low junction underlying the second surface.

In a method according to embodiments of the present disclosure, wherein the semiconductor substrate comprises a first p-n junction (or a first high-low junction) underlying the first surface and a second p-n junction (or a second high-low junction) underlying the second surface, extracting the recombination characteristic may comprise determining a total saturation current density at high injection for each metal coverage from a slope of inverse effective lifetime versus injection level, performing a correction of the effective lifetimes for Auger recombination, and afterwards extracting the saturation current density at a metallized surface and the saturation current density at a non-metallized surface from a slope of a linear fit of the total saturation current density versus metal coverage.

In embodiments of the present disclosure, the semiconductor substrate may be a silicon substrate, although the present disclosure is not limited thereto.

The method may further comprise correcting the measured injection levels and/or correcting the measured effective lifetimes taking into account the influence of metal conductivity, before extracting the recombination characteristics.

Methods of the present disclosure may advantageously be used for determining recombination characteristics of (passivated) emitter contacts and/or (passivated) base contacts of photovoltaic cells.

It is a potential advantage of methods of the present disclosure that recombination characteristics may be determined as a function of injection level. This may, for example, provide an indication of how well contact passivation performs at both low and high illumination intensities.

It is a potential advantage of methods of the present disclosure that the injection level may be measured together with the recombination characteristics, e.g., the injection level may be obtained from the photo-conductance measurement itself. It is a potential advantage of being able to measure the injection level that accurate recombination characteristics may be extracted.

It is a potential advantage of methods of the present disclosure that there may be no need to have a finished device for enabling the determination of recombination characteristics. This allows determining the recombination characteristics at different stages of device processing.

Certain objects and advantages of various inventive aspects have been described herein above. Of course, it is to be understood that not necessarily all such objects or advantages may be achieved in accordance with any particular embodiment of the disclosure. Thus, for example, those skilled in the art will recognize that the disclosure may be embodied or carried out in a manner that achieves or optimizes one advantage or group of advantages as taught herein without necessarily achieving other objects or advantages as may be taught or suggested herein. Further, it is understood that this summary is merely an example and is not intended to limit the scope of the disclosure. The disclosure, both as to organization and method of operation, together with features and advantages thereof, may best be understood by reference to the following detailed description when read in conjunction with the accompanying drawings.

BRIEF DESCRIPTION OF THE FIGURES

FIG. 6 shows the effective $J_{0,diel}$ incorporating the effect of bulk recombination and recombination in the passivated (non-metallized) emitter as a function of injection level.

FIG. 7 shows the effective $J_{0,diel}$ incorporating the effect of bulk recombination and recombination in the non-metallized back surface field region as a function of injection level.

FIG. 8 shows the difference between the surface recombination velocity at the metal contacts and the surface recombination velocity at the non-metallized surfaces.

FIG. 9 shows the effective $S_{diel}$ incorporating the effect of bulk recombination and recombination at non-metallized surfaces as a function of injection level.

Figure 1:
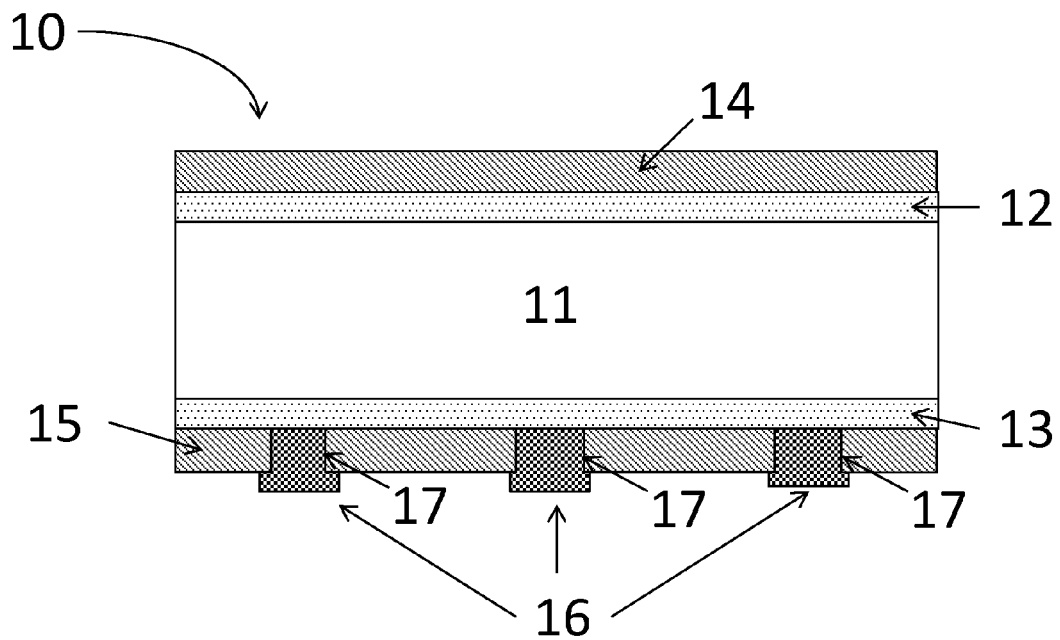
FIG. 1 schematically shows a cross section of an example a test structure that may be used in a method according to the present disclosure.

Any reference signs in the claims shall not be construed as limiting the scope of the present disclosure.

In the different drawings, the same reference signs refer to the same or analogous elements.

DETAILED DESCRIPTION

In the following detailed description, numerous specific details are set forth in order to provide a thorough understanding of the disclosure and how it may be practiced in particular embodiments. However, it will be understood that the present disclosure may be practiced without these specific details. In other instances, well-known methods, procedures and techniques have not been described in detail, so as not to obscure the present disclosure.

The present disclosure will be described with respect to particular embodiments and with reference to certain drawings but the disclosure is not limited thereto but only by the claims. The drawings described are only schematic and are non-limiting. In the drawings, the size of some of the elements may be exaggerated and not drawn on scale for illustrative purposes. The dimensions and the relative dimensions do not necessarily correspond to actual reductions to practice of the disclosure.

Furthermore, the terms first, second, third and the like in the description and in the claims, are used for distinguishing between similar elements and not necessarily for describing a sequential or chronological order. The terms are interchangeable under appropriate circumstances and the embodiments of the disclosure can operate in other sequences than described or illustrated herein.

Moreover, the terms top, bottom, over, under and the like in the description and the claims are used for descriptive purposes and not necessarily for describing relative positions. It is to be understood that the terms so used are interchangeable under appropriate circumstances and that the embodiments of the disclosure described herein are capable of operation in other orientations than described or illustrated herein.

The term "comprising", used in the claims, should not be interpreted as being restricted to the means listed thereafter; it does not exclude other elements or steps. Rather, the term should generally be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting of or including only components A and B.

The present disclosure provides methods based on photoconductance decay measurements for the determination of recombination characteristics, such as saturation current densities, recombination currents, surface recombination velocities or effective lifetimes, at a metallized semiconductor surface. In a method of the present disclosure, recombination characteristics are extracted from effective lifetime measurements as a function of metal contact fraction, using a dedicated test structure.

It is generally believed that recombination current measurements at metal-semiconductor contacts cannot be performed by means of a photo-conductance decay method, because the metal layer of such metal contact is dominant over the semiconductor substrate conductance. It is believed that only when using a very thin (e.g., 1 nm to 10 nm thickness) metal layer, photo-conductance measurements are feasible.

In methods of the present disclosure, the measurement of recombination characteristics at metallized semiconductor surfaces or metal contacts by means of photo-conductance decay is enabled by using a novel test structure. A test structure used in a method of the present disclosure comprises a semiconductor substrate with a predetermined metal pattern on at least one of the semiconductor substrate surfaces. In the further description, the focus is on test structures with a metal pattern on one semiconductor surface, but the present disclosure is not limited thereto and test structures having a metal pattern at both semiconductor surfaces may be used.

The test structures have a patterned metal layer in contact with the semiconductor, e.g., silicon, surface at predetermined locations, to enable the measurement of recombination characteristics at metal contacts by means of a photo-conductance decay method. The test structures allow covering parts of a semiconductor substrate or semiconductor wafer with a thick metal layer, while ensuring that the conductivity of the test structure remains dominated by the conductivity of the semiconductor substrate. As a result, minority carrier properties may be probed despite the metal coverage. In the context of this disclosure, a metal layer is considered as being thick if its sheet resistance is much smaller than the sheet resistance of the semiconductor substrate (wafer) on which it is provided.

It is a potential advantage of using such a predetermined metal pattern that there may be no need for providing a very thin metal layer (e.g., 1 nm thin) as in some known methods. The patterned metal layer may be in direct physical contact with the semiconductor surface, or a thin passivation layer (e.g., having a thickness less than about 5 nm) may be present between the patterned metal layer and the semiconductor surface (passivated contact).

The test structures of the present disclosure comprise at least two, preferably more than two, zones with different metal coverage, thus allowing performing measurements as a function of metal contact fraction (metal coverage).

The semiconductor substrate of a test structure in accordance with the present disclosure may have a p-n junction or a high/low junction underlying the semiconductor surfaces. The recombination characteristics of the metallized junctions may preferably be described by a saturation current density, but can also be described by an (effective) surface recombination velocity. An effective surface recombination velocity includes recombination at the semiconductor-metal interface, recombination in the diffused region, and recombination in the space charge region between the diffused region and the bulk of the substrate. In the absence of an underlying junction, the recombination characteristics at the metallized surface may preferably be described by a surface recombination velocity.

The present disclosure is further described for embodiments wherein the semiconductor substrate is a crystalline silicon substrate. However, the present disclosure is not limited thereto, and other semiconductor materials may be used.

A cross section of an example of a test structure 10 that may be used in a method according to the present disclosure is shown in FIG. 1. The test structure comprises a silicon substrate 11 of a first dopant type with a first doped region 12 at a first side and a second doped region 13 at a second side of the substrate. The first doped region 12 and the second doped region 13 may have a doping type opposite to the doping type of the substrate 11, thus forming p-n junctions underlying the substrate surfaces. In one example, the first doped region 12 and the second doped region 13 have the same doping profile. In alternative structures, the first doped region and the second doped region may have the same doping type as the substrate and a higher doping concentration, thus forming high-low junctions. At the first side of the substrate 11 a first surface passivation layer 14, such as a silicon oxide passivation layer, is present, covering the entire surface in the example shown. At the second side of the substrate 11 a second passivation layer 15, such as a silicon oxide passivation layer, is present. In the example shown, the second passivation layer 15 covers the entire surface of the substrate 11 at the second side, apart from locations where dedicated local openings 17 are provided through the second passivation layer 15. The test structure 10 further comprises a patterned metal layer, the patterned metal layer comprising a plurality of metal features 16, each of the metal features 16 being provided at the location of a local opening 17 through the second passivation layer 15, and in contact with the underlying silicon. As illustrated in FIG. 1, the metal features 16 may overlap the edges of the passivation layer 15 at the local openings 17. The test structure 10 thus comprises metal contact areas (areas with metallized surface), where the metal features 16 are in electrical contact with the silicon, and passivated or non-metallized areas/surfaces, where the passivation layer 14, 15 is in contact with the silicon surface (no electrical contact with a metal feature). The metal features may be in direct physical contact with the silicon or there may be a thin passivation layer (tunneling layer) in between, resulting in passivated contacts as described above.

Figure 2:
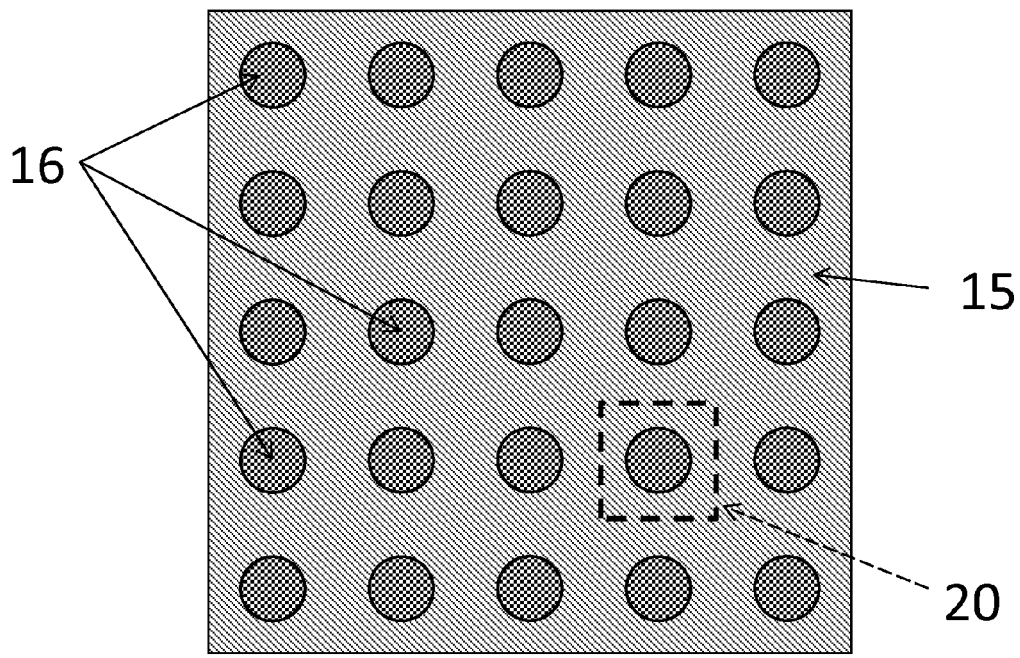
FIG. 2 shows a bottom view of the test structure of FIG. 1, illustrating a single zone of the test structure.

In embodiments of the present disclosure, the metal features 16 may, for example, have a circular shape or a square shape, or any other suitable shape. FIG. 2 shows a bottom view of the test structure of FIG. 1, with circular metal features. FIG. 2 shows 25 circular metal features to illustrate the concept, but in practice the number of metal features may be much higher, such as in the range of between about $10^5$ and $10^6$ metal features, e.g., spread over an area of about 4 cm by 4 cm, although the present disclosure is not limited thereto.

As illustrated in FIG. 2, the different metal features 16 are physically separated from one another. In a test structure of the present disclosure, a characteristic size of the metal features 16 is smaller than the effective minority carrier diffusion length in the metal covered area of the silicon substrate. The characteristic size may be the diameter in case of circular metal features or a side length in case of square metal features. This condition results in an approximately constant minority carrier concentration throughout the test structure and therefore enables a simpler interpretation of the measurements (as further described). In addition, in a test structure of the present disclosure, the spacing (distance) between neighboring metal features 16 is much smaller than the effective diffusion length in the passivated (non-metallized) area of the silicon substrate.

In a test structure of the present disclosure, both the lateral size of the metal features and the distance between neighboring metal features are typically in the sub-millimeter range.

FIG. 2 only shows a single zone of a test structure, with a single metal coverage. Test structures of the present disclosure may comprise at least two, preferably more than two, zones with different metal coverage, e.g., with a different ratio between the contacted area (metallized surface area) and the total zone area. A test structure of the present disclosure may, for example, comprise a plurality of square zones, each of the zones having a different metal coverage. Providing zones with different metal coverage enables separating information on recombination in the non-metallized areas from information related to recombination in metal covered areas. Preferably, the test structure comprises more than two different zones, such as nine different zones, each zone having a different metal coverage. Each zone may have a size in the order of several square centimeters, such as 4 cm×4 cm. Preferably, each zone of the test structure is composed of a two-dimensional array of identical unit cells 20, as indicated in FIG. 2, the present disclosure not being limited thereto.

Typical coil frequencies used during radio-wave detected contactless photo-conductance decay measurements are in the 11 MHz range, which corresponds to probing the wafer under test with electromagnetic radiation with a wavelength of about 27 m. Since the wavelength of the radiation by which the test structure is probed is many orders of magnitudes larger than the characteristic size of the metal pattern on the wafer, the equivalent resistance that is observed by the radiation may be found from ordinary electric circuit theory. No wave effects need to be taken into account.

Figure 3:
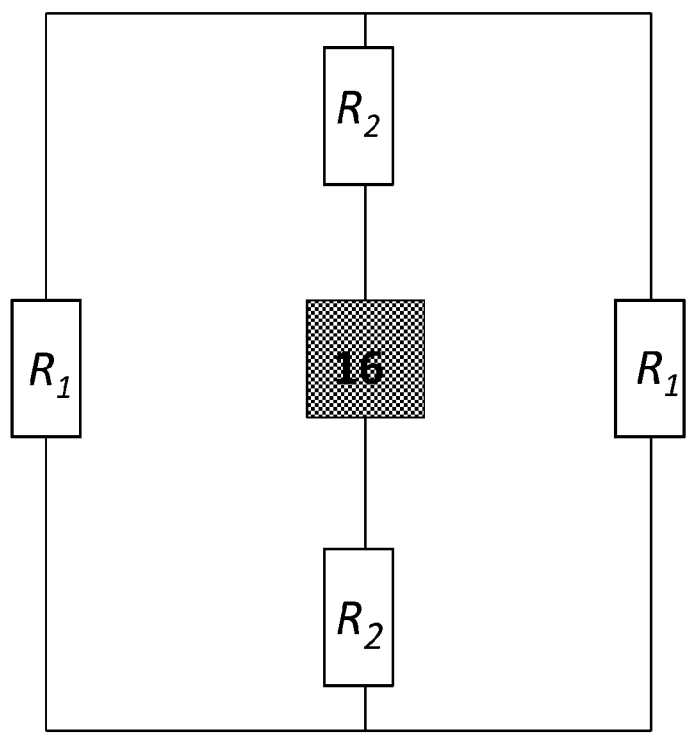
FIG. 3 illustrates an equivalent circuit for a unit cell of a test structure of the present disclosure with square metal features.

From ordinary electric circuit theory, an approximate expression for the influence of the presence of metal features 16 on the test structure conductivity may be derived. An estimation of the influence of metal conductivity on the resistance of the wafer can be obtained by using the equivalent circuit shown in FIG. 3 for a unit cell 20 of a test structure of the present disclosure with square metal features 16. Each unit cell 20 (as indicated in FIG. 2, for example) of a zone of the test structure can be considered as being composed of a first area which is not contacted by metal (but covered by the passivation layer 15) and a second area which is locally shorted by a metal feature 16. Perfect local shunting is assumed in this example. The electrical resistance of the metal layer is assumed to be much smaller than the electrical resistance of the silicon substrate 11. The impedance due to the capacitance between metal features 16 is assumed to be much larger than the impedance due to the conductivity of the substrate 11 between metal features. The resistances $R_1$, $R_2$ shown in the equivalent circuit of FIG. 3 are then given by:

$$R_1 = \frac{2R_{s,Si}S}{S-d} \text{ and} \tag{1}$$

$$R_2 = \frac{R_{s,Si}S}{2d} \tag{2}$$

wherein S is the pitch of the metal features, d is the length of the sides of the square metal features and $R_{s,Si}$ is the sheet resistance of the silicon wafer. The sheet resistance $R_s$ of the metallized wafer is then given by:

$$R_s = R_{s,Si} \frac{1 - C_{met}}{1 + C_{met}^{3/2}} \tag{3}$$

wherein $C_{met}$ is the metal coverage fraction given by the ratio between the metal contacted area and the total area of a unit cell.

In case of circular metal features the sheet resistance $R_s$ of the metallized wafer is approximately given by:

$$R_s = R_{s,Si}\left[1 + \frac{4C_{met}}{\pi - 2\sqrt{\pi C_{met}}}\right]^{-1} \tag{4}$$

Measured photo-conductance data may be corrected to obtain the wafer conductance. The correction factor depends on the test structure geometry. For a test structure comprising an array of circular metal dots, wafer conductivity $\sigma_{Si}$ is related to the measured conductivity $\sigma_{meas}$ by equation (5).

$$\sigma_{meas} = \sigma_{Si}\left[1 + \frac{4C_{met}}{\pi - 2\sqrt{\pi C_{met}}}\right] \tag{5}$$

For a test structure comprising an array of square metal dots, wafer conductivity $\sigma_{Si}$ is related to the measured conductivity $\sigma_{meas}$ by equation (6).

$$\sigma_{meas} = \sigma_{Si}\frac{1 + C_{met}^{3/2}}{1 - C_{met}} \tag{6}$$

Further corrections may be applied to take into account the effect of non-zero contact resistance between the metal and the semiconductor. Finite contact resistance causes local shorting of the device under test to be imperfect. More specifically, it approximately takes a transfer length $L_T$ for current to flow from the semiconductor to the metal, wherein the transfer length equals contact resistance divided by sheet resistance. The transfer length effect can approximately be taken into account by considering that the effective metal dot size is approximately reduced by twice the transfer length: one transfer length for the current to flow from semiconductor to metal and one transfer length for current to flow back again. Thus:

$$d_{eff} = d - 2L_T \tag{7}$$

For circular dots, metal coverage is given by:

$$C_{met} = \frac{\pi d^2}{4S^2} \tag{8}$$

Substituting d by $d_{eff}$ then yields the effective metal coverage that influences wafer conductivity when the presence of contact resistance results in imperfect shorting of the substrate:

$$C_{eff} = \frac{\pi(2 - 2L_T)^2}{4S^2} = C_{met}\left(1 - \frac{L_T}{d} + 2\left[\frac{L_T}{d}\right]^2\right) \tag{9}$$

$C_{met}$ can be substituted by $C_{eff}$ to estimate the effect of finite contact resistance on correction factors due to metal coverage. Similar expressions may be derived for test structures comprising an array of metal dots with a different shape, such as an array of square metal dots. These corrections are only applicable if $L_t$ is smaller than d. If $L_t$ is much larger than the characteristic size d, the effect of local shunting due to the presence of metal may be negligible.

In a method of the present disclosure, the recombination characteristics are extracted from effective lifetime measurements as a function of metallized area coverage using test structures as described above, and using photo-conductance decay measurements. For substrates or test structures with two areas $A_1$, $A_2$ with different recombination rates per unit area $R_1$, $R_2$, the total recombination rate R is the area-weighted sum of the recombination rates in the two areas if the recombination rate is constant throughout each area. This may be expressed as follows:

$$R = \frac{A_1}{A}R_1 + \frac{A_2}{A}R_2 \quad (10)$$

A test structure used in a method of the present disclosure has two such areas with different recombination characteristics. In the further description, a test structure as shown in FIG. 1 is assumed.

The first area is a two-side passivated region, e.g., having a Si—SiO$_2$ interface at both surfaces. The recombination rate in the first area is given by equation (11), wherein $R_{diel}$ is the recombination rate at a passivated (non-metallized) surface and $R_{bulk}$ is the recombination rate in the silicon bulk of the test structure. It is further assumed that passivated areas have the same surface passivation at both sides.

$$R_1 = 2R_{diel} + R_{bulk} \quad (11)$$

The second area of the test structure has the same surface passivation as the first area on a first side of the substrate and has different recombination characteristics at the second side of the substrate. At the second side, the surface in the second area may for example comprise a silicon-air interface, a silicon-metal interface, or silicon-passivated contact interface. A passivated contact can, for example, comprise a dielectric-metal stack, a dielectric-polysilicon-metal stack, or an amorphous silicon-metal stack, the present disclosure not being limited thereto. The recombination rate in the second area of a test structure of the present disclosure is given by equation (12), wherein $R_{met}$ is the recombination rate at the silicon-metal interface.

$$R_2 = R_{diel} + R_{met} + R_{bulk} \quad (12)$$

Assuming that the recombination rate per unit area in the bulk of both areas and the recombination rate per unit area at the non-metallized surfaces are equal in both areas, the total recombination rate for a test structure of the present disclosure may be written as given in equation (13).

$$R = R_{bulk} + 2R_{diel} + C_{met}[R_{met} - R_{diel}] \quad (13)$$

wherein $C_{met}$ is the metal coverage: $C_{met} = A_2/A$.

Therefore, in a method of the present disclosure, the difference between the recombination rate at the metallized and passivated (non-metallized) surfaces ($R_{met} - R_{diel}$) can be extracted from the slope of the recombination rate R versus metal surface coverage fraction $C_{met}$.

The method of the present disclosure is further described, for example, wherein the substrate is an n-type silicon wafer having at both sides a p-type diffused region (emitter region). It is assumed that the injection level is constant over the substrate thickness (in the bulk of the substrate), and over the entire substrate area. This is a reasonable assumption for wafers with an emitter region (or a back surface field region) at the front side and at the back side if the wafer thickness and the contact opening size (size of the metal features) are both much smaller than the minority carrier diffusion length.

Emitter recombination $R_{emitter}$ can be described by a saturation current density $J_{0,emitter}$ that is defined by:

$$R_{emitter} = \frac{J_{0,emitter}}{qn_i^2}\Delta p(N_D + \Delta p) \quad (14)$$

in which a recombination mechanism characterized by an ideality factor one is assumed. $\Delta p$ is the injection level at the bulk-side of the space charge region between emitter and bulk and $N_D$ is the doping concentration in the bulk of the wafer.

Bulk recombination is described by an effective lifetime:

$$R_{bulk} = \Delta p W/\tau_{bulk} \quad (15)$$

wherein W is the distance between the emitter space charge regions at the first side and at the second side of the test structure, which is approximately equal to the substrate thickness. It is assumed that the bulk injection level $\Delta p$ is constant over the wafer thickness. This is the case if the bulk minority carrier diffusion length is much larger than the wafer thickness.

From the total recombination rate R (as given in (13)), a global effective lifetime $\tau_{eff}$ is defined: $R = \Delta p W/\tau_{eff}$. This yields the following expression for $\tau_{eff}$:

$$\frac{1}{\tau_{eff}} = \frac{1}{\tau_{bulk}} + J_{0,tot}\frac{N_D + \Delta p}{qn_i^2 W} \quad (16)$$

$$\frac{1}{\tau_{eff}} = \frac{1}{\tau_{bulk}} + 2J_{0,diel}\frac{N_D + \Delta p}{qn_i^2 W} + C_{met}[J_{0,met} - J_{0,diel}]\frac{N_D + \Delta p}{qn_i^2 W} \quad (17)$$

$J_{0,met}$ is the saturation current density of the metallized emitter of the test structure, $J_{0,diel}$ is the saturation current density of the passivated (non-metallized) emitter of the test structure, and $J_{0,tot}$ is the total emitter saturation current density of the test structure. $\tau_{eff}$ is the global effective lifetime of the test structure, $\tau_{bulk}$ is the minority carrier lifetime in the bulk of the wafer, $N_D$ is the doping concentration in the bulk of the wafer, and $\Delta p$ is the injection level in the bulk of the wafer. The injection level is assumed to be constant over the wafer thickness in the bulk of the wafer and in the plane of the test structure. q is the electron charge, $n_i$ is the intrinsic carrier density, and W is the wafer thickness (more accurately: the distance between the space charge regions of both emitter regions).

At arbitrary injection levels, $J_{0,met} - J_{0,diel}$ can be extracted from the slope of the inverse effective lifetime ($1/\tau_{eff}$) measured by photo-conductance decay versus metal coverage ($C_{met}$). Both $\tau_{eff}$ and $\Delta p$ are the quantities extracted from the photo-conductance measurements. Both may need to be corrected for local shunting due to the presence of metal features before they are used to calculate recombination parameters. As further described, for steady state and generalized photo-conductance measurements, both injection level and lifetime need to be corrected. For transient measurements, only the injection level needs to be corrected.

Based on (17), an upper limit of $J_{0,diel}$ can be extracted from the intercept of inverse effective lifetime ($1/\tau_{eff}$) versus metal coverage ($C_{met}$) with the $C_{met}=0$ axis.

In high injection ($\Delta p \gg N_D$), $J_{0,tot}$ can be extracted from the slope of $1/\tau_{eff}$ as a function of injection level. After correction for Auger-recombination, $\tau_{bulk}$ is assumed to be independent of injection level. Therefore, $J_{0,met}$ and $J_{0,diel}$ can be extracted from $J_{0,tot}$ versus metal coverage data, irrespective of the relative magnitude of bulk recombination and recombination at the passivated surface:

$$J_{0,tot}=2J_{0,diel}+C_{met}[J_{0,met}-J_{0,diel}] \quad (18)$$

Equations (3) and (4) show that even though the resistance of the test structures of the present disclosure remains dominated by the silicon substrate, metal coverage does have an influence on the resistance of the wafer. This results in an influence on the measured injection levels during photo-conductance measurements and on the measured effective lifetimes. The influence on measured effective lifetime depends on the mode in which the conductivity measurement is done, as described below.

Without going through the detailed derivation, it can be shown that the relation between measured injection level $\Delta p_{measured}$ and actual injection level $\Delta p_{real}$ is approximately given by equation (19) for a test structure comprising circular metal features, and by equation (20) for a test structure comprising square metal features.

$$\Delta p_{real} = \Delta p_{measured}\left[1+\frac{4C_{met}}{\pi-2\sqrt{\pi C_{met}}}\right]^{-1} \quad (19)$$

$$\Delta p_{real} = \Delta p_{measured}\frac{1-C_{met}}{1+C_{met}^{3/2}} \quad (20)$$

Therefore, the injection level is over-estimated in photo conductance measurements on partly metal covered wafers due to local shunting by the metal layers.

The effect of errors in measured injection levels on errors in extracted minority carrier lifetimes depends on whether photo-conductance measurements are performed in a transient mode, steady state mode or generalized mode. It is assumed that the behavior of majority carriers is fully determined by the minority carrier concentration and the requirement of charge neutrality. The continuity equation for minority carriers (holes) is considered without taking into account trapping effects:

$$q\frac{\delta p}{\delta t} = -\nabla J_p + q(G-R) \quad (21)$$

For calculating the influence of wafer shorting due to the partial metal coverage on extracted effective lifetimes, it is assumed that the current is slowly varying such that its gradient is negligible compared to the net recombination term. For negligible current gradients, and explicitly writing the recombination current in terms of the excess minority carrier concentration and an effective lifetime, equation (21) becomes:

$$\frac{\delta p}{\delta t} = G - \frac{\Delta p}{\tau_{eff}} \quad (22)$$

Recognizing that the time-rate of change of minority carrier concentration equals the time-rate of change of the excess minority carrier density, this equation can be written in terms of effective lifetime as:

$$\frac{1}{\tau_{eff}} = \frac{G}{\Delta p} - \frac{1}{\Delta p}\frac{\delta \Delta p}{\delta t} \quad (23)$$

wherein $\tau_{eff}$ is an effective lifetime and G is the generation rate, being defined as the number of minority carriers generated in the wafer per second and per unit volume. Therefore, misinterpretations of the injection level may result in errors on the measured effective lifetimes and a correction may need to be made.

Depending on the time rate of change of the excess minority carrier density compared to the generation rate, either a transient analysis (wherein the minority carrier lifetime is much longer than the characteristic decay time of the generation term), a steady state analysis (wherein the characteristic decay time of the generation term is much longer than the minority carrier lifetime), or a generalized analysis applies.

In a transient analysis, the generation term decays much faster than the characteristic time in which minority carrier concentration changes. Equation (23) then becomes:

$$\frac{1}{\tau_{eff}} = -\frac{1}{\Delta p}\frac{\delta \Delta p}{\delta t} \quad (24)$$

In combination with equation (19) this yields:

$$\frac{1}{\tau_{measured}} = \frac{1}{\Delta p_{real}}\frac{\delta p_{real}}{\delta t} \quad (25)$$

Therefore, shorting of the wafer by metal coverage has no influence on measured effective lifetimes, as long as the extent of shorting is not injection level dependent. However, if the metal contact area fraction is not taken into account, the injection level is underestimated. The latter does have an indirect effect on extracted saturation currents when effective lifetimes depend on injection level. Not taking local shorting due to metal into account results in overestimation of injection levels.

In a steady state analysis, changes in excess minority carrier densities are assumed to occur in much faster time scales than characteristic changes of generation terms. Measured effective lifetimes are then given by:

$$\frac{1}{\tau_{measured}} = \frac{G}{\Delta p_{measured}} \quad (26)$$

Similarly, the actual effective lifetimes are given by:

$$\frac{1}{\tau_{real}} = \frac{G}{p_{real}} \quad (27)$$

Combination of equations (26), (27) and (19) yields an approximate relation between real and measured effective lifetimes as a function of metal coverage, obtained from steady-state photo-conductance measurements. For a test structure with circular metal dots this is approximately given by equation (28); for a test structure with square metal dots this is approximately given by equation (29).

$$\tau_{real} = \tau_{measured}\left[1 + \frac{4C_{met}}{\pi - 2\sqrt{\pi C_{met}}}\right] \quad (28)$$

$$\tau_{real} = \tau_{measured}\frac{1 - C_{met}}{1 + C_{met}^{3/2}} \quad (29)$$

Therefore, the presence of metal results in over-estimation of minority carrier lifetimes extracted from steady-state photo-conductance measurements and an appropriate correction is needed.

In case of a generalized analysis, the functional relation between real and measured effective lifetimes extracted from photo conductance measurements may be found by means of a similar derivation.

Although the method of the present disclosure is described above mainly for the determination of saturation currents on test structures with p-n junctions, the method may also be used for determining recombination characteristics on test structures without p-n junctions. For example, for samples with high-low junctions ($n^+$-n junctions or $p^+$-p junctions) or for samples without any junction, recombination characteristics at metallized surfaces may also be measured using a test structure of the present disclosure. For this case, inverse effective lifetime is given as a function of metal coverage as:

$$\frac{1}{\tau_{eff}} = \frac{1}{\tau_b} + \frac{2S_p}{W} + \frac{C_m}{W}(S_m - S_p) \quad (30)$$

wherein $\tau_{eff}$ is the effective lifetime, $\tau_b$ is a bulk minority carrier lifetime, $S_p$ is the effective surface recombination velocity at the passivated (non-metallized) surface, $S_m$ is the effective surface recombination velocity at the metal covered surface, and $C_m$ is the metal coverage and W is wafer thickness. From equation (30) the difference between effective surface recombination velocity at the metal covered surface and at the passivated surface can be extracted as a function of injection level.

The test structure of the present disclosure may also be used to determine effective lifetimes instead of saturation current densities or surface recombination velocities. In this case:

$$\frac{1}{\tau_{eff}} = \frac{1}{\tau_p} + C_{met}\left[\frac{1}{\tau_m} - \frac{1}{\tau_p}\right] \quad (31)$$

wherein $\tau_{eff}$ is an effective lifetime for the entire test structure (e.e., the measured quantity as a function of metal coverage), $\tau_p$ is the effective lifetime in passivated (non-metallized) areas, and $\tau_m$ is the effective lifetime in metal covered areas.

Methods of the present disclosure may advantageously be used for saturation current density extraction of metallized emitters of photovoltaic cells, for example.

Using methods of the present disclosure, saturation current extraction was performed for test structures with Al contacts on diffused boron emitters. In addition, using methods of the present disclosure, recombination characteristics were determined for test structures with Al contacts on test structures comprising high/low junctions (e.g., as in a back surface field region of photovoltaic cells) and for test structures without any diffused regions. All measurements were done using a steady state analysis.

Semi-square 156 mm×156 mm, 150 to 160 micrometer thick n-type Cz Si wafers with a bulk resistivity of 3 to 8 Ohm-cm were used in the experiments. An experimental split was made between: (a) wafers with an emitter diffusion ($p^+$ diffusion forming a p-n junction at both wafer sides); (b) wafers with a back surface field diffusion ($n^+$ diffusion forming a high-low junction at both wafer sides); and (c) wafers without any diffusion. A thermally grown silicon oxide layer was used as a passivation layer.

For the saturation current measurements, each passivated wafer was divided into nine zones, in which different fractions $C_{met}$ were provided. Circular openings with 15 micrometer diameter were lithographically defined and etched through the passivation layer. The nominal coverage of the exposed region ranged from between about 0% to 17% (e.g., 0%, 1.25%, 2.5%, 5%, 7.5%, 10%, 12.5%, 15%, and 17%). Due to possible over-etching or under-etching and/or over-development or under-development during lithographical definition of the contact openings, the actual coverage may be somewhat different. The distance between the openings varied between 118.9 micrometer for the zone with 1.25% coverage and 32.2 micrometer for the zone with 17% coverage. In all zones, circular metal dots with a diameter of 15 micrometer were used. A 0.5 micrometer thick Al layer was subsequently sputtered on the wafer and etched such that only the exposed silicon regions remained covered. Then a forming gas anneal was done.

Effective lifetime measurements were performed on these test structures in accordance with a method of the present disclosure. For each of the nine zones with different metal coverage of the test structure a quasi-steady state photoconductance (QSSPC) measurement was done. Each QSSPC measurement yields effective lifetimes as a function of injection level. Thus, results are obtained as a function of metal coverage and as a function of injection level.

Figure 4:
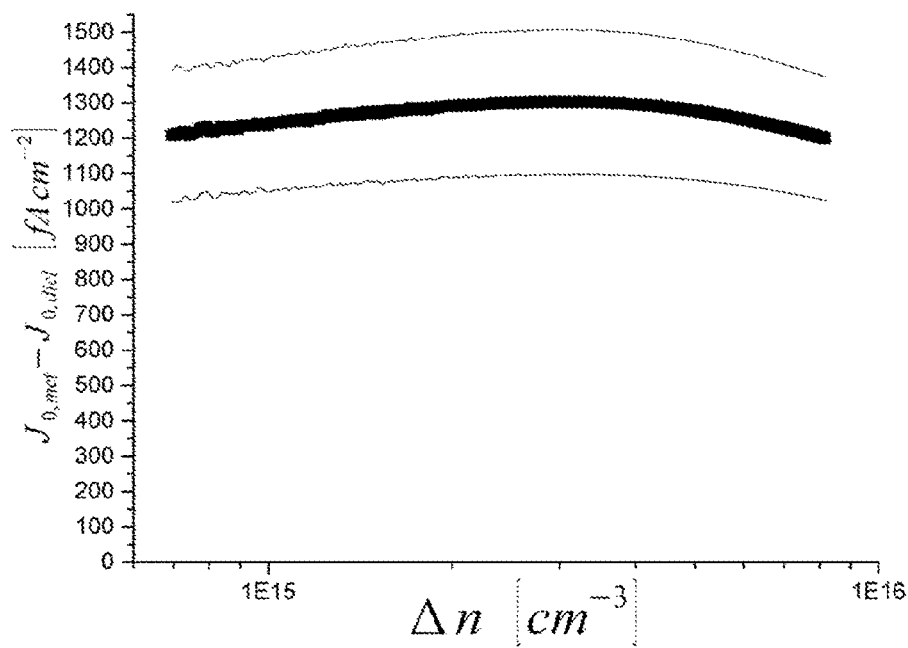
FIG. 4 shows the difference between the saturation current density of a metallized emitter and the saturation current density of a non-metallized emitter as a function of injection level, as determined using a method of the present disclosure on a test structure with p-n junctions. Illustrated error bars are 95% confidence intervals.

FIG. 4 shows the difference between the saturation current density $J_{0,met}$ of the metallized emitter and the saturation current density $J_{0,diel}$ of the non-metallized emitter as a function of injection level, as determined using a method according to the present disclosure. Error bars are 95% confidence intervals. For emitters with good surface passivation and with non-passivated metal contact as in the test structure used in the experiment, it may be assumed that $J_{0,met}$ is much larger than $J_{0,diel}$, therefore $J_{0,met} - J_{0,diel} \approx J_{0,met}$. Therefore, the data shown in FIG. 4 can be considered as a lower limit for the saturation current density of the metallized emitter. These results were obtained by first measuring the effective lifetime as a function of injection level for different metal coverages and then extracting the saturation current density from the slope for the different injection levels. In the results shown, injection levels and effective lifetimes have been corrected for local shorting due to the presence of metal features as described above, before extracting saturation current densities from the measurements.

Figure 5:
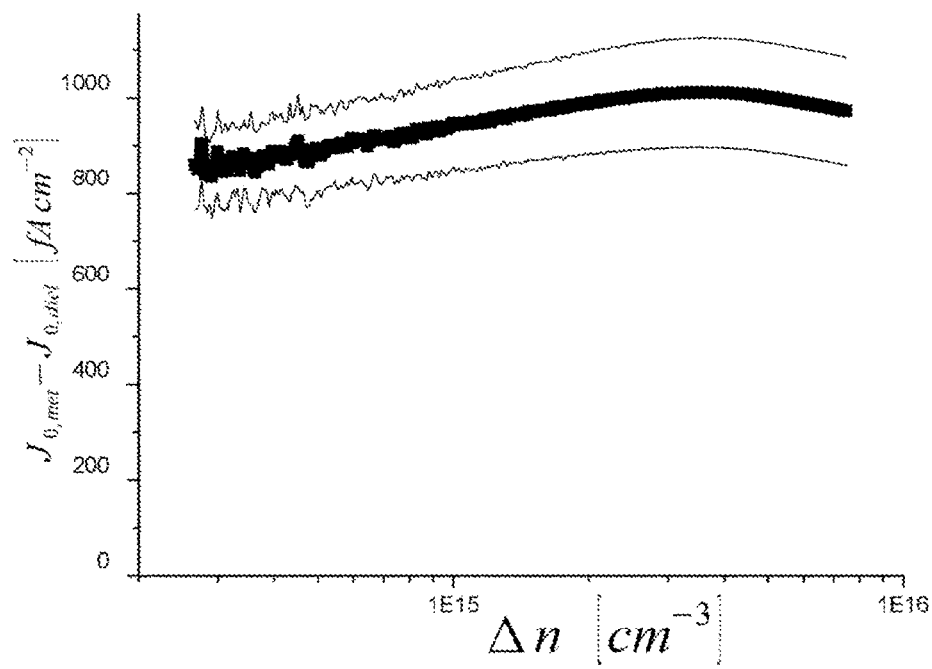
FIG. 5 shows the difference between the saturation current density of a metallized back surface field region and the saturation current density of a non-metallized back surface field region as a function of injection level, as determined using a method of the present disclosure on a test structure with high-low junctions. Illustrated error bars are 95% confidence intervals.

FIG. 5 shows the difference between the saturation current density of the metallized back surface field region and the saturation current density of the non-metallized back surface field region as a function of injection level, as in FIG. 4, but for a test structure with a high-low junction instead of a p-n junction at both sides of the wafer.

Figure 6:
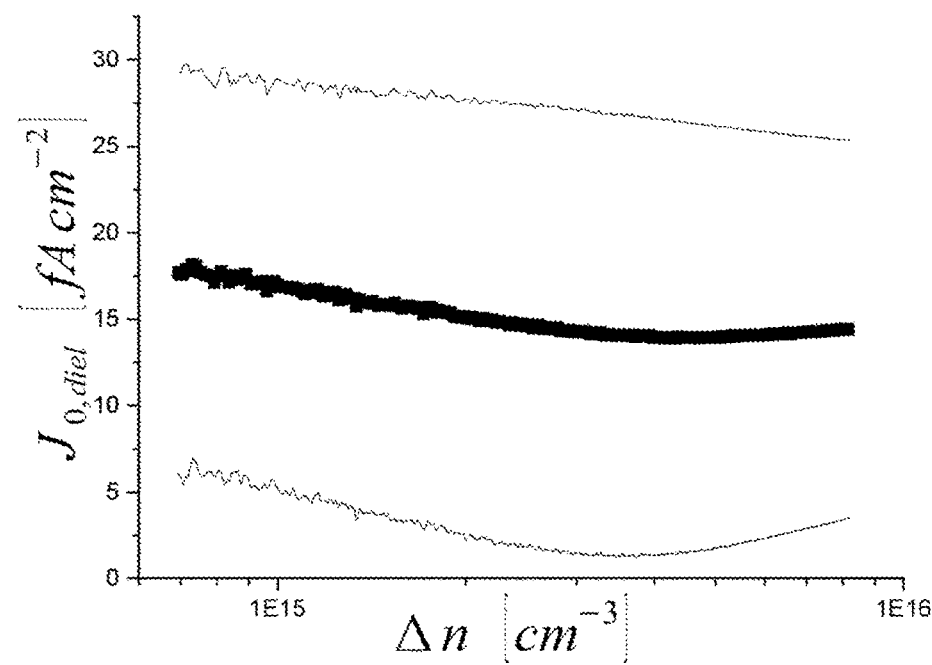
FIG. 6 shows the extracted saturation current density for test structures with an emitter at both sides in accordance with a method of the present disclosure.

FIG. 6 shows the extracted saturation currents for test structures with an emitter diffusion at both sides of the test structure. FIG. 6 shows the effective $J_{0,diel}$ incorporating the effect of bulk recombination and recombination in the passivated (non-metallized) emitter. The $J_{0,diel}$ shown in FIG. 6 was extracted from the intercept with the $C_{met}=0$ axis of a linear fit of inverse effective lifetime versus metal coverage for different injection levels. In general, the intercept has a contribution from bulk recombination and a contribution from recombination in the passivated emitter. It was assumed that the bulk recombination component is negligible compared to the recombination component in the passivated emitter. Therefore, the estimate for $J_{0,diel}$ shown in FIG. 6 is an upper limit for $J_{0,diel}$ since there is a (small) contribution from bulk recombination which was not taken into account.

Figure 7:
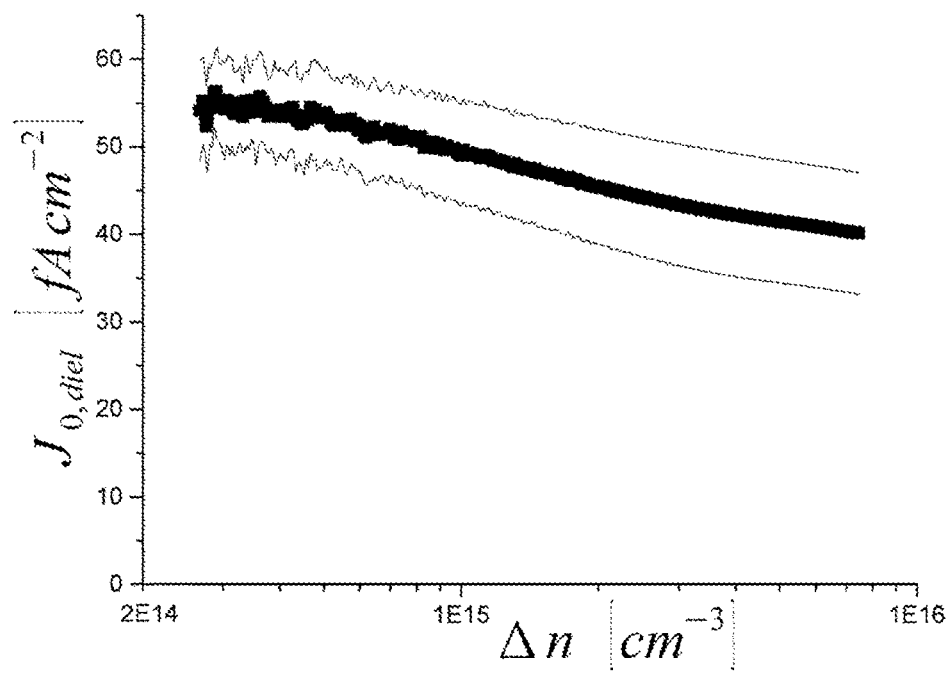
FIG. 7 shows the extracted saturation current density for a test structure with a back surface field region (n-type high/low junction) at both sides.

FIG. 7 shows the extracted saturation current density for test structures with a back surface field region (high-low junction) at both sides. FIG. 7 shows the effective $J_{0,diel}$ incorporating the effect of bulk recombination and recombination in the non-metallized back surface field region as a function of injection level, as in FIG. 6 extracted from the intercept with the $C_{met}=0$ axis of a linear fit of inverse effective lifetime versus metal coverage for different injection levels.

Figure 8:
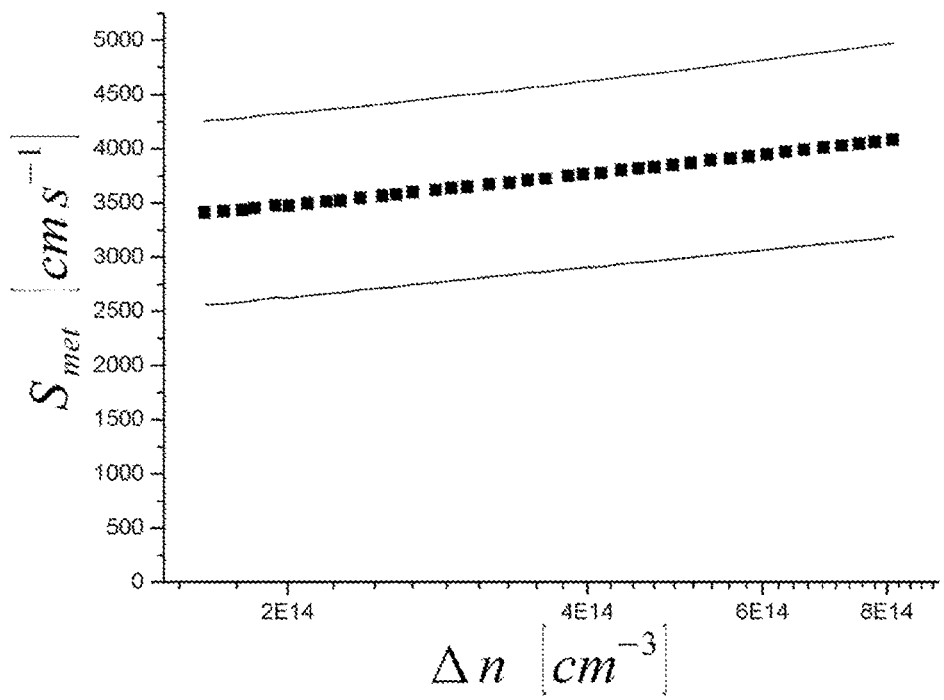
FIG. 8 shows the extracted surface recombination velocity for a test structure without junctions wherein the metal directly contacts the bulk of the silicon wafer.

FIG. 8 shows the difference between the surface recombination velocity at the metal-semiconductor interface $S_{met}$ and the surface recombination velocity at the non-metallized semiconductor surface $S_{diel}$ as a function of injection level for test structures without diffused regions. Error bars are 95% confidence intervals. For samples with good surface passivation and with non-passivated metal contacts as in the test structure used in the experiment, it may be assumed that $S_{met}$ is much larger than $S_{diel}$, therefore $S_{met}-S_{diel} \approx S_{met}$. The values shown in FIG. 8 can therefore be considered as a lower limit for $S_{met}$. These results were obtained by first measuring the effective lifetime as a function of injection level for different metal coverages and then extracting the surface recombination velocity from the slope for the different injection levels. In the results shown, injection levels and effective lifetimes have been corrected for local shorting due to the presence of metal features as described above, before extracting saturation current densities from the measurements. The extracted surface recombination velocities shown here are most likely an underestimation because the injection level at the silicon-metal interface is most likely significantly lower than the average injection level due to the high recombination rate at that surface.

Figure 9:
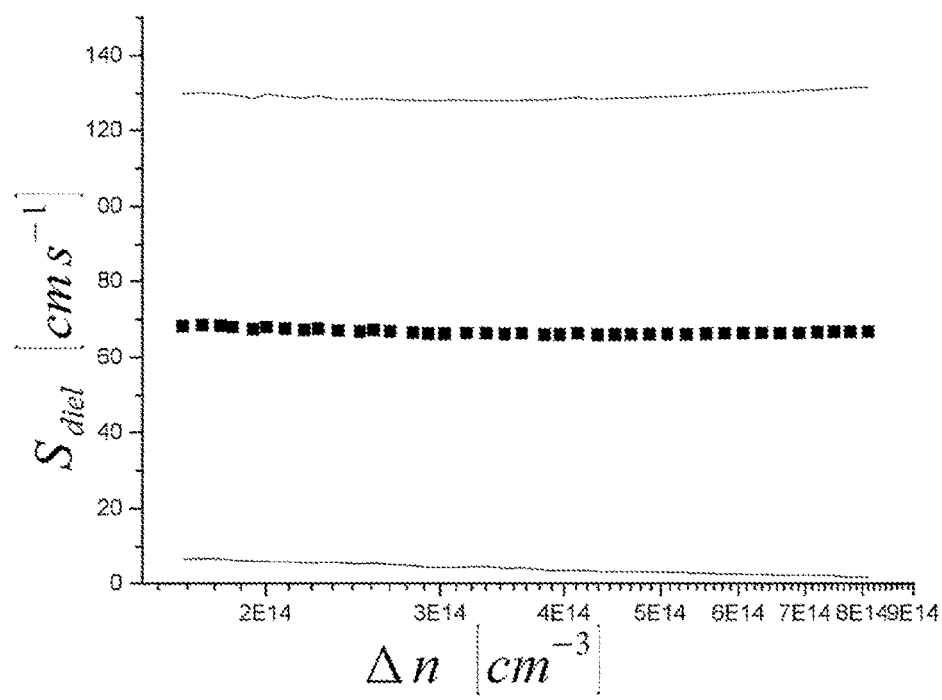
FIG. 9 shows the extracted surface recombination velocity for a test structure without diffusions in accordance with a method of the present disclosure.

FIG. 9 shows the extracted surface recombination velocity for test structures without a diffused region. FIG. 9 shows the effective $S_{diel}$ incorporating the effect of bulk recombination and recombination at the non-metallized surfaces as a function of injection level, extracted from the intercept with the $C_{met}=0$ axis of a linear fit of inverse effective lifetime versus metal coverage for different injection levels.

Figure 10:
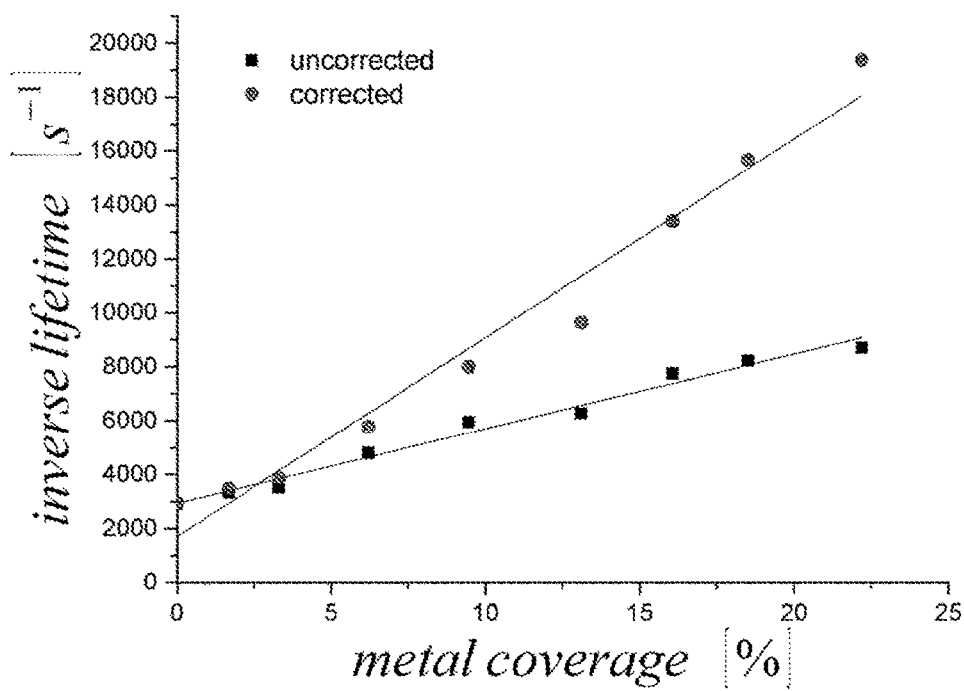
FIG. 10 shows the inverse effective lifetime as a function of metal coverage, at an injection level of $7.10^{15}$ cm$^{-3}$, extracted on a test structure in accordance with the present disclosure, before (squares) and after (dots) correction for local shunting due to the presence of metal. The test structure comprises an n-type silicon wafer with a p$^+$ type emitter diffusion at both sides.

FIG. 10 shows the inverse effective lifetime as a function of metal coverage for a sample with an emitter diffusion at both sides. FIG. 10 shows both the as-measured effective lifetime and the effective lifetime that was corrected for the effect of local shorting due to the presence of the metal, at an injection level of $7.10^{15}$ cm$^{-3}$. It can be seen that the correction for local shunting due to the presence of metal increases the slope of inverse effective lifetime versus metal coverage.

In accordance with embodiments of the present disclosure, effective lifetime measurements may be interpreted in several ways:

i. For samples with an emitter region (e.g., with a p-n junction) or a back surface field region (e.g., with a high-low junction), $J_{0,tot}$ may be extracted in high injection for each metal coverage from the slope of inverse effective lifetime versus injection level. Then $J_{0,met}$ and $J_{0,diel}$ may be independently extracted from a linear fit of $J_{0,tot}$ versus metal coverage.

ii. For samples with an emitter region (e.g., with a p-n junction) or a back surface field region (e.g., with a high-low junction), $[J_{0,met}-J_{0,diel}]$, a lower estimate for $J_{0,met}$ and an upper estimate for $J_{0,diel}$ may be extracted for all injection levels from a linear fit of inverse effective lifetime versus metal coverage.

iii. Alternatively, measurements may be interpreted in terms of surface recombination velocities. For each injection level, $[S_{met}-S_{diel}]$ and an upper estimate for $S_{diel}$ may be extracted from a linear fit of inverse effective lifetime versus metal coverage. This approach may also be used for test structures without any diffused region.

iv. For non-ideal samples, for each injection level $[1/\tau_m - 1/\tau_p]$ and $1/\tau_p$ may be extracted from a linear fit of inverse effective lifetime versus metal coverage.

The foregoing description details certain embodiments of the disclosure. It will be appreciated, however, that no matter how detailed the foregoing appears in text, the disclosure may be practiced in many ways. It should be noted that the use of particular terminology when describing certain features or aspects of the disclosure should not be taken to imply that the terminology is being re-defined herein to be restricted to including any specific characteristics of the features or aspects of the disclosure with which that terminology is associated.

While the above detailed description has shown, described, and pointed out novel features of the disclosure as applied to various embodiments, it will be understood that various omissions, substitutions, and changes in the form and details of the device or process illustrated may be made by those skilled in the technology without departing from the disclosure.

The invention claimed is:

1. A method for determining a recombination characteristic at a semiconductor surface, wherein the method comprises:
   providing a test structure, wherein the test structure comprises:
      a semiconductor substrate having a first surface and a second surface opposite to the first surface;
      a first passivation layer on the first surface;
      a second passivation layer on the second surface, the second passivation layer having a plurality of openings at predetermined locations; and
      a plurality of metal features in contact with the second semiconductor surface at the predetermined locations, thus forming metallized surfaces at the predetermined locations and non-metallized surfaces outside the predetermined locations,
   wherein a characteristic size of the metal features is smaller than an effective diffusion length in the underlying semiconductor at the predetermined locations, and the metal features being provided with a spacing smaller than an effective diffusion length in the underlying semiconductor outside the predetermined locations, the metal features being grouped in a plurality of zones, each of the plurality of zones having a different metal coverage, the metal coverage being the ratio between the metallized surface area and the total area;

performing a photo-conductance decay measurement in each of the plurality of zones, thereby determining effective lifetimes for different injection levels as a function of metal coverage; and extracting the recombination characteristic from the determined effective lifetimes.

2. The method according to claim 1, wherein extracting the recombination characteristic from the determined effective lifetimes comprises determining a difference between the recombination characteristic at a metallized surface and the recombination characteristic at a non-metallized surface for each of the injection levels from a slope of a linear fit of inverse effective lifetime versus metal coverage.

3. The method according to claim 1, wherein extracting the recombination characteristic comprises determining an upper value of the recombination characteristic at a non-metallized surface for each of the injection levels from an intercept of a linear fit of inverse effective lifetime versus metal coverage with a zero metal coverage axis.

4. The method according to claim 1, wherein the recombination characteristic is a surface recombination velocity.

5. The method according to claim 1, wherein the recombination characteristic is a saturation current density.

6. The method according to claim 1, wherein the recombination characteristic is an inverse lifetime.

7. The method according to claim 1, wherein the semiconductor substrate comprises a first doped region forming a first p-n junction underlying the first surface and a second doped region forming a second p-n junction underlying the second surface, and wherein the recombination characteristic is a saturation current density.

8. The method according to claim 1, wherein the semiconductor substrate comprises a first p-n junction underlying the first surface and a second p-n junction underlying the second surface, and wherein extracting the recombination characteristic comprises:

determining a total saturation current density at high injection for each metal coverage from a slope of inverse effective lifetime versus injection level;

performing a correction of the effective lifetimes for Auger recombination; and afterwards extracting the saturation current density at a metallized surface and the saturation current density at a non-metallized surface from a slope of a linear fit of the total saturation current density versus metal coverage.

9. The method according to claim 1, wherein the semiconductor substrate comprises a first doped region forming a first high/low junction underlying the first surface and a second doped region forming a second high/low junction underlying the second surface, and wherein the recombination characteristic is a saturation current density.

10. The method according to claim 1, wherein the semiconductor substrate comprises a first high/low junction underlying the first surface and a second high/low junction underlying the second surface, and wherein extracting the recombination characteristic comprises:

determining a total saturation current density at high injection for each metal coverage from a slope of inverse effective lifetime versus injection level;

performing a correction of the effective lifetimes for Auger recombination; and afterwards extracting the saturation current density at a metallized surface and the saturation current density at a non-metallized surface from a slope of a linear fit of the total saturation current density versus metal coverage.

11. The method according to claim 1, wherein the semiconductor substrate is a silicon substrate.

12. The method according claim 1, further comprising correcting the determined injection levels and effective lifetimes taking into account the influence of metal conductivity, before extracting the recombination characteristic.

13. The method according to claim 1, wherein the first passivation layer is a continuous layer covering the first surface.

14. The method of claim 1, wherein the extracted recombination characteristic is of one or more of a emitter contact or a base contact of a photovoltaic cell.

* * * * *